United States Patent [19]

Nathan et al.

[11] 4,196,729
[45] Apr. 8, 1980

[54] DEVICE FOR PERFUSING A HEART WITH BLOOD SUPPLIED AT CONSTANT PRESSURE

[76] Inventors: Ira M. Nathan, Old Forge Dr., Carmel, N.Y. 10512; Joseph N. Cunningham, 3 Washington Sq., New York, N.Y. 10012

[21] Appl. No.: 863,647

[22] Filed: Dec. 23, 1977

[51] Int. Cl.² .............................................. A61M 1/03
[52] U.S. Cl. ............................. 128/214 E; 128/214 F
[58] Field of Search ........... 128/214 R, 214 E, 214 F, 128/214 B, 1

[56] References Cited

U.S. PATENT DOCUMENTS

| | | | |
|---|---|---|---|
| 3,896,803 | 7/1975 | Mason | 128/214 R |
| 3,946,731 | 3/1976 | Lichtenstein | 128/214 R |
| 4,080,966 | 3/1978 | McNally et al. | 128/214 E |

*Primary Examiner*—Robert E. Bagwill
*Attorney, Agent, or Firm*—Blum, Kaplan, Friedman, Silberman & Beran

[57] ABSTRACT

An apparatus for perfusing the heart of a patient with oxygenated blood detects the blood pressure at the point of supply, usually the aortic root or a coronary blood vessel, and transmits this pressure to a pressure switch which controls a solenoid valve for recycling blood driven by a roller pump to the oxygenator, or, selectively, through a surge tank and to the point of supply within the patient's vascular system. The surge tank has an air cushion therein for holding essentially constant the pressure at which the blood is supplied to the patient, and, thus, for holding constant the pressure at the point of supply.

The system is fail-safe since the pressure switch can be connected to the solenoid so that blood is pumped to the surge tank and thence to the patient in the event of the failure of an electrical connection to the solenoid valve.

Provision is made for continuous feed of blood to the patient at a greater-than-normal rate should an emergency arise or for cutting off the flow of blood to the patient when desired.

21 Claims, 4 Drawing Figures

DEVICE FOR PERFUSING A HEART WITH BLOOD SUPPLIED AT CONSTANT PRESSURE

BACKGROUND OF THE INVENTION

It is now standard procedure to perfuse the heart of a patient undergoing cardiac surgery with blood by any of a number of techniques. Most commonly, blood is supplied at essentially constant rate, the rate being adjustable in accordance with the observed condition of the patient. This type of supply procedure introduces difficulties where the patient's blood pressure may be varying as the result of beating of the heart, and attempts have been made to modify the feed rate to correlate with systolic and diastolic pressures in the vascular system.

A preferred method is to feed the blood at such a rate that the blood pressure in the aortic root or in a coronary blood vessel is held at a selected value. One difficulty which has been encountered arises from the fact that there is a pressure drop in the supply tube, the size of this pressure drop depending upon the flow rate of blood through the tube so that accurate determination of the pressure at the point of supply becomes difficult. Further difficulties arise from the fact that every possible contingency must be provided for, especially power failure. As is evident, then, a system which can supply blood in a mode consistent with the best interests of the patient, which is simple and inexpensive as well as light in weight, and which can provide protection for the patient against virtually any type of failure is greatly to be desired.

SUMMARY OF THE INVENTION

An apparatus for supplying blood to a patient, in its principal mode of function, supplies blood at such a rate as to hold the blood pressure at the point of supply within limits selected by the surgeon. A sensor is provided for determining the blood pressure at the point of supply and a pressure switch connected with the sensor controls a solenoid valve for recycling blood from an oxygenated-blood supply tank back to the tank or alternatively toward the patient. A surge tank between the solenoid valve and the point of supply has an air cushion above the blood in the lower portion of said surge tank. The surge tank eliminates sudden changes in blood-flow rate which would otherwise be present since the compressed air-cushion above the blood in the tank continues to transfer blood to the point of supply, but at a gradually decreasing rate, when the solenoid valve is in a condition such that blood from the supply tank is recycled thereto.

In a preferred form, the pressure switch is connected with the solenoid valve so that in the event of loss of power to the solenoid valve, the solenoid valve will be in a condition such that blood is transferred from the supply tank to the surge tank and thence to the patient. Consequently, loss of power to the solenoid valve cannot result in loss of blood supply to the patient.

The preferred pump means is a roller pump, this type of pump having been found suitable for the transfer of blood through a tube without degradation of the blood itself. The roller pump is so constructed that it can be manually operated, thus providing against loss of electrical power to the entire system. Also, the capacity of the roller pump should be at least twice the usual optimum rate of supply to the patient and preferably up to about 5 times as great as the usual optimum rate, such high rates of blood supply being desired in certain types of emergencies.

In general, the point of supply is the aortic root or a coronary artery. In one embodiment of the invention separate cannulas are utilized for determining blood pressure proximate the point of supply and for introducing blood at the point of supply. In another embodiment of the invention, these two cannulas are combined, one lying within the other.

Accordingly, an object of the present invention is a fail-safe apparatus for delivering blood to the cardiac area of a patient at a rate such as to hold the pressure at said cardiac area within a selected range.

Another object of the present invention is a fail-safe apparatus for delivering blood to the cardiac area of a patient utilizing a first cannula for determining the blood pressure in the cardiac area of the patient and a second cannula for introducing blood to the cardiac area of the patient.

A further object of the present invention is a fail-safe apparatus for delivering blood to the cardiac area of a patient utilizing a pressure switch for controlling a solenoid valve between either of two conditions, the solenoid valve in a first condition recycling blood from a blood supply tank back to the tank and in a second condition transferring blood toward said cardiac area.

Still another object of the present invention is a fail-safe apparatus for supplying blood to the cardiac area of a patient, said apparatus including a surge tank having an air cushion above blood in the lower part thereof for eliminating sudden changes in flow rate as a solenoid valve changes condition.

An important object of the present invention is a fail-safe apparatus for supplying blood to the cardiac area of a patient, said apparatus including a pressure switch electrically connected with a solenoid valve for controlling the condition thereof, said electrical connection being such that a failure in the connection conditions the valve so that blood is transferred toward the patient.

A significant object of the present invention is a fail-safe apparatus for supplying blood to the cardiac area of a patient wherein the primary transfer means is a roller pump designed to be manually operable in the event of power failure and having a capacity several times that normally required, said excess capacity being useful in the event of certain types of surgical emergencies.

Still other objects and advantages of the invention will in part be obvious and will in part be apparent from the specification The invention accordingly comprises the features of construction, combinations of elements, and arrangement of parts which will exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
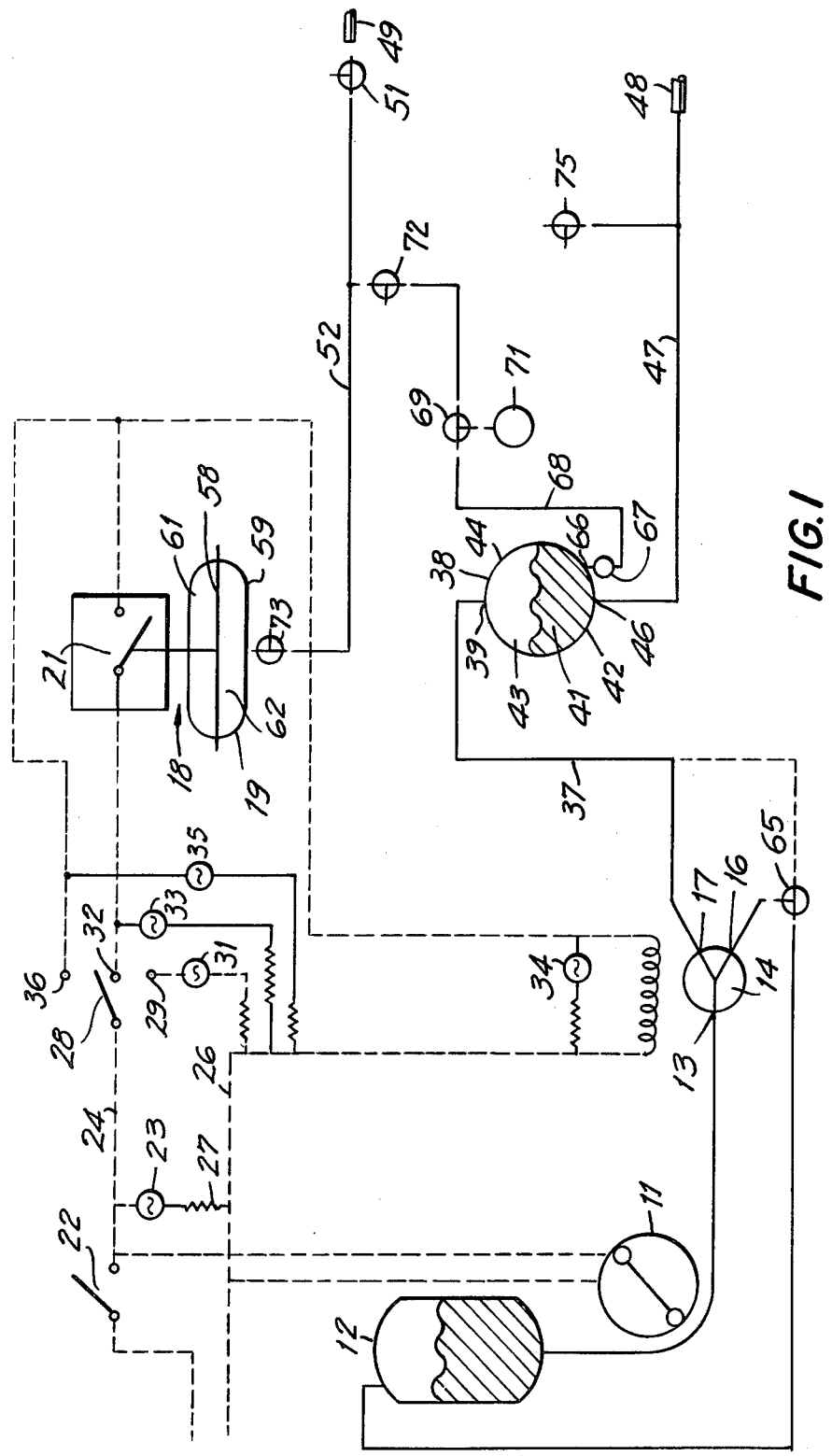
FIG. 1 shows diagrammatically the blood-supply apparatus of the present invention.

The apparatus disclosed herein is constructed and arranged primarily for supplying blood to the cardiac area of a patient under conditions such that the blood pressure proximate the point of supply remains within limits selected by the surgeon. It should be noted that, in contrast to the prior art, it is the blood pressure which is selectively controlled and not the feed rate. Nevertheless, the feed rate is controlled in such a way as to maintain the blood pressure proximate the point of supply within said selected limits. Moreover, the feed rate is adjusted automatically without sudden changes, and without "hunting" in the control system, thereby eliminating rapid wear of the control elements. As shown in FIG. 1, roller pump 11 transfers oxygenated blood from supply tank 12 to port 13 of solenoid valve 14. Solenoid valve 14, in preferred form, is a three-way valve having exit ports 16 and 17. In first condition, the blood passing through said solenoid valve 14 is recycled through exit port 16 back to supply tank 12. In second condition, said solenoid valve 14 transfers the blood through exit port 17 toward the patient.

Solenoid valve 14 is under the control of pressure switch indicated generally by the reference numeral 18, said pressure switch consisting of a pressure transducer which may be a displacement diaphragm, as shown in FIG. 1, and an electric switch 21. As shown in FIG. 1, electric switch 21 is mechanically coupled to pressure transducer 19. This arrangement is satisfactory where pressure transducer 19 is a pressure diaphragm as shown in FIG. 1. However, pressure transducer 19 can also be a variable capacitor or a strain gauge or a variable inductance, in which case a relay or other appropriate accessories are provided as well known to those skilled in the art.

Preferably, pressure switch 18 is so connected electrically with solenoid valve 14 that in the absence of an electric signal to the solenoid valve, i.e., when the solenoid valve is non-energized, the valve is in a condition such that entry port 13 is connected with exit port 17, in other words, so that blood is transferred toward the patient rather than recycled to surge tank 12.

Roller pump 11, pressure switch 18 and solenoid valve 14 may be powered from an external source (not shown), connection being made thereto through main switch 22. That power is being supplied to the apparatus is shown by the indicator lamp 23 connected in series with resistor 27 across hot line 24 and ground 26. That power is reaching roller pump 11 is shown by the same indicator lamp 23.

Power to pressure switch 18 passes through mode selector switch 28 which can be set for operation of the apparatus in any of three modes. When mode selector switch 28 is positioned to make contact at point 29, the blood flows continuously under the drive of roller pump 11 toward the point of supply for perfusing the heart. This mode of delivery serves both for filling the system with blood and for high-rate delivery where such high-rate delivery is necessary for meeting an emergency. It will be noted that pressure switch 18 is by-passed when mode selector switch 28 makes contact with point 29, this position being indicated by neon-glow lamp 31 and its associated resistor. As a result, solenoid valve 14 is non-energized when mode selector switch 28 is at position 29.

Mode selector switch 28 is brought into contact with point 32 to place the apparatus in normal operational condition, power then being supplied to pressure switch 18 and, depending upon the condition of pressure switch 18, to solenoid valve 14. Indicator lamp 33 shows when power is being supplied to pressure switch 18 and indicator lamp 34 shows whether solenoid valve 14, under the control of pressure switch 18, is in energized or non-energized condition.

Throwing mode-selector switch 28 to point 36 by-passes pressure switch 18 and provides power continuously to solenoid valve 14, thereby connecting entry port 13 with exit port 16 for recycling of blood from and to supply tank 12. Movement of switch 28 to position 36 cuts off the blood supply to the patient without shutting down the apparatus. Movement of switch 28 to position 36 is indicated by indicator lamp 35. The fact that the solenoid valve 14 is in the continuously-energized condition is shown by indicator lamp 34. This mode of operation is provided since the surgeon at certain stages of the surgical procedure may require that the supply of blood to the patient be suspended or the pressure be reduced.

In the transfer of blood from solenoid valve 14 to the patient, the blood traverses conduit 37 and enters surge tank 38 through port 39. Since the blood pressure at the point of supply to the patient is substantially above atmospheric, usually about 80 mm of mercury, resistance to flow of blood to the point of supply results in compression of the air initially present in surge tank 38 and development of a pool of blood 41 in the lower part 42 of said surge tank. The air or other gas 43 in upper part 44 is compressed by introduction of blood driven by roller pump 11 until it rises sufficiently above the pressure at the point of supply so that flow of blood for perfusing the heart begins.

However, the pressure at the aortic root varies with a specific patient so that the general pressure level should be adjustable over a range between about 50 to 150 mm. Also, during one phase of the cardiac cycle (systolic), blood flow slows or stops due to constriction of coronary vessels. The heart therefore receives a pulsating flow under normal conditions. The flow occurs when the heart is in the relaxed phase (diastolic), that is, when the heart is not pumping. Accordingly, the apparatus disclosed herein simulates natural flow, since when the pressure drops in the aortic root, the flow rate increases, and vice versa.

For reasons which will be presented below, the total volume of surge tank 38 is preferably between about 2 and 5 liters.

Blood leaves surge tank 38 through exit port 46 and traverses conduit 47 to a cannula 48 indicated only diagrammatically in FIG. 1. This cannula is preferably placed in the aortic root of the patient or, alternatively, in a coronary artery.

Figure 2:
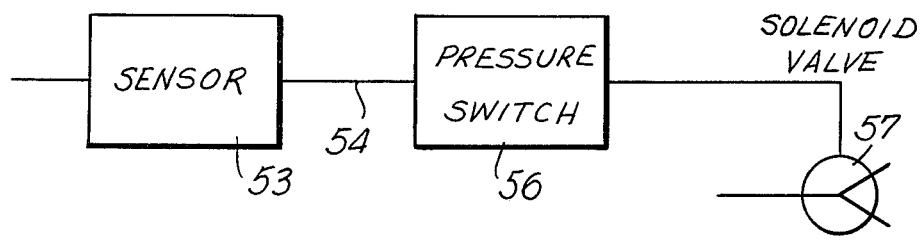
FIG. 2 is a block diagram showing how the condition of a solenoid valve may be controlled in response to the pressure sensed in the cardiac area of a patient and thereby to control the rate of flow of blood to the patient.

As pressure-sensing means, a second cannula 49 is provided for entry into the aortic root, said cannula 49 functioning as a sensor. Cannula 49 is connected through three-way valve 51 and conduit 52 to pressure switch 18. The combination of sensor, pressure switch and solenoid valve is shown more generally in FIG. 2 in schematic form. As shown in FIG. 2, sensor 53 is operatively connected by connecting means 54 to pressure switch 56 which controls solenoid valve 57 in accordance with the signal received from pressure switch 56. Connecting means 54 can be hydraulic, pneumatic, mechanical or electrical, depending upon the nature of sensor 53 and pressure switch 56.

In the embodiment of pressure switch 18 shown in FIG. 1, the pressure transducer 19 consists essentially of a displacement diaphragm 58 dividing a housing 59 into first chamber 61, maintained at atmospheric pressure, and second chamber 62 which holds a pressure corresponding to that of the cardiac region proximate the point of supply. It will be noted that in general, no blood enters conduit 52 since this portion of the system has only a single opening, namely that at the end of cannula 49. Conduit 52 may be filled with fluid compatible with blood.

Pressure transducer 19, preferably has a dead-band of about 10 mm, the dead-band being the difference in pressure between an upper limit at which pressure switch 18 is closed and a lower limit at which said switch is open. Preferably, the range over which the pressure switch operates can be adjusted either upwardly or downwardly to maintain the pressure at the point of supply at any desired level.

The presence of the dead-band in the pressure switch prevents hunting, that is, frequent cycling of the pressure switch and, as a consequence, of solenoid valve 14. Frequent change in the condition of solenoid valve 14 is undesirable since it causes trauma to the blood and, of course, is associated with wear of the switch as well as wear of the solenoid valve itself. A cycle time of about one minute is desirable and appropriate in that trauma to the blood and wear of the device are minimized and yet the variation in blood pressure at the point of supply is small. The combination of a dead-band of about 10 mm and a total volume of about 3 liters for the surge tank provides this cycle time. As is evident, other combinations of dead-band and surge tank volume can also be found to provide an appropriate cycle time.

The way in which the surge tank minimizes changes in supply rate and blood pressure at the point of supply can be seen from the nature of an air-cushion. Considering the situation when blood is being supplied to the surge tank and thence to the patient at a rate such that the blood pressure at the point of supply is rising, said blood pressure eventually rises to the point where the selected upper pressure limit for closing pressure switch 18 is reached. Power is then supplied to solenoid valve 14 connecting entry port 13 of said valve to exit port 16 and the blood transferred by roller pump 11 from supply tank 12 is recycled to same. Although the supply of blood to surge tank 38 is thus interrupted, air-cushion 43 is still at a pressure high enough so that flow of blood from surge tank 38 to the point of supply continues. As the flow of blood continues, the volume of the air-cushion increases and the pressure of the air decreases. The decrease in flow of blood to the point of supply causes a decrease in the blood pressure at the point of supply. However, the blood pressure at the point of supply is being continuously monitored by sensor 49 and when the pressure at this point drops below the lower pressure limit at which pressure switch 18 is opened, the solenoid valve becomes de-energized and supply of blood to surge tank 38 is re-initiated.

It is significant that there is a pressure drop between surge tank 38 and the point of supply, this pressure drop resulting from flow through conduit 47 and cannula 48, cannula 48 necessarily being relatively small in diameter. It is this pressure drop which is responsible for the pressure in tank 38 being sufficiently greater than the blood pressure at the point of supply so that flow continues, although at a decreasing rate, when the solenoid valve is in a condition such that blood supply to the surge tank is interrupted. Further, there is no pressure drop between sensor 49 and pressure switch 18 because there is no flow between these points. Accordingly, even when pressure transducer 19 is of the displacement diaphragm type the pressure in chamber 62 corresponds closely to that at the point of supply.

Figure 3:
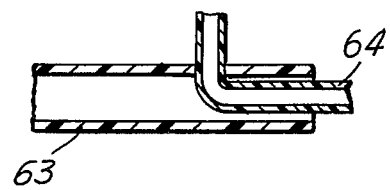
FIG. 3 is a sectional view of a double cannula requiring only a single point of entry for both sensing the blood pressure at the point of supply and for introducing blood at the point of supply.

In certain cases it is desirable that the number of openings made in the patient be minimized. For this purpose, a double cannula as shown in FIG. 3 can be used. FIG. 3 shows schematically the entry end of such a double cannula, outer tube 63 being connected for introducing blood in the patient and inner tube 64 serving for sensing the pressure at the point of supply in a manner corresponding to that of sensor 49.

Figure 4:
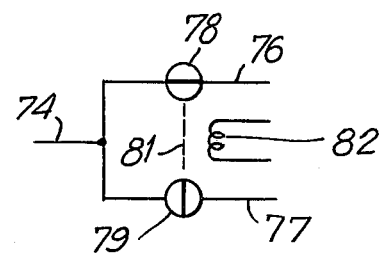
FIG. 4 is a diagrammatic view of two 2-way valves arranged to function as a 3-way valve.

The apparatus of FIG. 1 is constructed and arranged for coping with contingencies in addition to that of failure of power at solenoid valve 14. Should the valve jam or lock in the condition such that entry port 13 is connected with exit port 16, manually-operable three-way valve 65 provides for transferring the blood to surge tank 38. Needless to say, although three-way valves are most convenient for making changes in flow paths, other valve combinations are possible, specifically a pair of two-way valves. Wherever the use of the three-way valve is specified, it is to be understood that this term also includes other valve combinations which provide the same flow control. Such a combination of 2-way valves is shown in FIG. 4 in which supply line 74 is connected to exit lines 76 and 77 through two-way valves 78 and 79 respectively. These valves may be linked together, as indicated by dashed line 81, so that only one of said valves is open at any given time. The valves may be operated by solenoid 82 connected to mode selector switch 28 and pressure switch 18.

A second exit port 66 in surge tank 38 leads through 2-way valve 67, conduit 68 and three-way valve 69 to pressure gauge 71. This makes it possible to monitor the pressure in surge tank 38 and to control the rate of supply of blood to the patient should pressure switch 18 fail in either the open or the closed position. In such circumstances, complete control can be provided by operating roller pump 11 manually at a rate such as to maintain the pressure in surge tank 38 at a level as read on pressure gauge 71. Alternatively, 3-way valve 69 can be set to register the pressure in conduit 52 on pressure gauge 71. If the pressure switch fails in the closed position, three-way valve 65 can be positioned manually for directing blood to surge tank 38.

As aforenoted, roller pump 11 should be of a capacity which is at least twice that normally required by a patient and preferably up to about 5 times that normally required. When the capacity is about twice that normally required, then the solenoid valve will be in the supply condition and in the recycle condition for approximately equal periods of each duty cycle. Although this is a desirable arrangement, situations may occur during surgical procedures in which a very rapid supply of blood is desired. For this purpose, it is preferable that the roller pump be capable of supplying up to about 5 times the normal rate. Increased blood-supply rate is needed in the event of a hyperemic reaction. Under such conditions, the blood flows out of the aortic root more rapidly than usual and the feed rate must increase to hold the blood pressure at a desired level. Where unusually rapid flow is desired, regardless of the specific pressure at the supply point, valves 67, 69 and 72 are positioned for transfer of blood from surge tank 38 to conduit 52 and thence through valve 51 and cannula 49 to the patient, thus providing a parallel flow path in addition to that through conduit 47 and cannula 48 for supply of blood to the patient. Valves 51, 72, 73 and 75 are used for back-filling lines, flushing lines and removing air from lines.

As will be seen from the above description, the introduction of surge tank 38 with its air-cushion serves a variety of purposes, these including elimination of surges in the rate of blood supply resulting from mismatch in the capacity of roller pump 11 and the demand of the patient, elimination of frequent cycling of the pressure switch, continuity of blood supply in the case of interruption of power and the possibility of parallel blood-supply lines. The entire apparatus is extremely simple since elaborate monitoring of the blood pressure or of blood flow rates is unnecessary, and yet protection for emergency situations and contingencies is provided. The apparatus can be constructed of readily available components which are relatively low in cost and the apparatus is, in addition, sufficiently light so that it is readily portable.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language might be said to fall therebetween.

What is claimed is:

1. Apparatus for perfusing the heart of a patient during cardiac surgery at a feed rate such as to hold the blood pressure at the point of supply to said patient within selected upper and lower limits above atmospheric, comprising:
    reservoir means for holding oxygenated blood;
    surge tank means for receiving blood from said reservoir means, holding said blood under a cushion of pressurized gas, the term "gas" being taken to include air, and transferring said blood to said point of supply;
    constant feed-rate pump means for transferring said blood from said reservoir means toward said surge tank means, said pump means having a blood-pumping rate substantially greater than that at which blood is to be supplied to said patient;
    sensing means for determining the blood pressure at said point of supply;
    controllable valve means for adjusting the rate of transfer of said blood from said reservoir means to said surge tank means;
    first conduit means for transferring said blood from said surge tank means to said point of supply, said first conduit means being sized to present sufficient resistance to the flow of blood therethrough that the pressure of said gas in said surge tank is substantially above that at said point of supply, thereby providing for immediate change in rate of flow of blood through said conduit means to compensate for change in blood pressure at said point of supply; and controller means operatively connected to said sensing means and to said valve means for increasing the rate of feed of blood to said surge tank means when said pressure drops below said lower limit and for decreasing said feed rate when said pressure rises above said upper limit, said controller means being adjustable to establish a desired pressure at the point of supply.

2. The apparatus as defined in claim 1, wherein said sensing means includes a first cannula for entering the vascular system of said patient proximate said point of supply, pressure-sensing means constructed and arranged for activating said controller means, and connecting means joining said first cannula and said pressure-sensing means for transmitting the pressure at said point of supply to said pressure-sensing means, said first conduit means including a second cannula for positioning at said point of supply.

3. The apparatus as defined in claim 2, wherein said sensing means and controller means are combined as pressure switch means.

4. The apparatus as defined in claim 3, wherein said pressure switch means is arranged and constructed for passing and interrupting an electric current, and said valve means comprises solenoid valve means connected to said pressure switch means for permitting and preventing the flow of blood from said reservoir means to said surge tank means in response to electric current from said pressure switch means.

5. The apparatus as defined in claim 4, wherein said solenoid valve means is movable between first and second conditions, said solenoid valve means in said first condition being connected for recirculating blood taken by said pump means from said reservoir means back to same, and in said second condition being connected for transferring blood from said reservoir means to said surge tank means.

6. The apparatus as defined in claim 5, wherein said pressure switch means is so connected with said solenoid valve means that said solenoid valve means is in said second condition when said pressure switch means is open so that no electric current flows to said solenoid valve means.

7. The apparatus as defined in claim 5, further comprising selector switch means having a first position for holding said solenoid valve means in said first condition for recycling of blood to said resevoir means independent of the pressure at said point of supply, a second position for control of said solenoid valve means by said controller means and a third position for holding said solenoid valve means in said second condition for continuous feed of blood to said patient independent of the pressure at said point of supply.

8. The apparatus as defined in claim 7, further comprising manually-operable valve means connected with said solenoid valve means for diverting blood from said solenoid valve means in the event of failure when in said first condition and away from said reservoir means and to said surge tank means, whereby blood can be supplied to said patient in the event of failure of said solenoid valve means while in said first condition.

9. The apparatus as defined in claim 4, wherein said solenoid valve means is a three-way valve.

10. The apparatus as defined in claim 4, wherein said solenoid valve means consists essentially of two interconnected two-way valves.

11. The apparatus as defined in claim 3, wherein said sensing means includes first tube means connecting said cannula with said pressure switch means, and comprising second tube means and surge-tank valve means connecting the lower portion of said surge tank means with said first tube means for supplying blood to said patient from said surge tank means through said first cannula as well as through said second cannula in the event that a greatly increased feed rate is desired.

12. The apparatus as defined in claim 2, wherein said sensing means is a pressure transducer.

13. The apparatus as defined in claim 2, wherein said sensing means comprises a housing and a displacement diaphragm dividing said housing into a first chamber held at atmospheric pressure and a second chamber joined to said connecting means.

14. The apparatus as defined in claim 2, wherein said sensing means is a strain gauge.

15. The apparatus as defined in claim 2, wherein said sensing means is one of a variable capacitance and a variable inductance joined to said connecting means for responding to the pressure transmitted thereby.

16. The apparatus as defined in claim 2, wherein said first cannula and said second cannula are concentric.

17. The apparatus as defined in claim 1, wherein said pump means has a maximum feed rate which is greater by a factor of about 2 to 5 than the average feed rate required by a patient.

18. The apparatus as defined in claim 1, wherein said pump means is a roller pump normally electrically-operated, and manually-operable in the event of a power failure.

19. The apparatus as defined in claim 1, wherein said upper and lower limits differ by about 10 mm of Hg.

20. The apparatus as defined in claim 1, wherein said point of supply is one of the aortic root and a coronary blood vessel of said patient.

21. The apparatus as defined in claim 1, wherein said surge tank means has a volume of about 2 to about 5 liters.

* * * * *